US009468481B2

(12) United States Patent
Klein (10) Patent No.: US 9,468,481 B2
(45) Date of Patent: Oct. 18, 2016

(54) ANTI-BACKOUT MECHANISM FOR ORTHOPEDIC DEVICES

(75) Inventor: James Klein, Dallas, TX (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 378 days.

(21) Appl. No.: 13/474,553

(22) Filed: May 17, 2012

(65) Prior Publication Data
US 2013/0310881 A1 Nov. 21, 2013

(51) Int. Cl.
*A61B 17/80* (2006.01)
*A61B 17/86* (2006.01)

(52) U.S. Cl.
CPC ....... *A61B 17/8047* (2013.01); *A61B 17/8605* (2013.01)

(58) Field of Classification Search
CPC .............. A61B 17/80; A61B 17/8033; A61B 17/8047; A61B 17/86; A61B 17/8605; A61B 17/861; A61B 17/862
USPC ................... 606/70, 71, 280–296, 300–321; 411/114, 119, 120
See application file for complete search history.

(56) References Cited

U.S. PATENT DOCUMENTS

| 3,630,252 | A | * | 12/1971 | Rosan et al. | 411/335 |
| 4,067,371 | A | * | 1/1978 | Stencel | 411/107 |
| 4,797,022 | A | * | 1/1989 | Crigger | 403/408.1 |
| 5,578,034 | A | | 11/1996 | Estes | |
| 6,227,782 | B1 | * | 5/2001 | Bowling et al. | 411/114 |
| 6,402,755 | B1 | * | 6/2002 | Pisharodi | 606/71 |
| 6,425,719 | B1 | * | 7/2002 | Staudt | 411/119 |
| 7,229,442 | B2 | * | 6/2007 | Schafer | 606/272 |
| 7,670,072 | B2 | * | 3/2010 | Tella et al. | 396/529 |
| 7,749,257 | B2 | * | 7/2010 | Medoff | 606/290 |
| 7,955,362 | B2 | * | 6/2011 | Erickson et al. | 606/289 |
| 8,388,666 | B2 | * | 3/2013 | Castaneda et al. | 606/290 |
| 2002/0110437 | A1 | * | 8/2002 | Kirimoto | 411/119 |
| 2004/0127896 | A1 | * | 7/2004 | Lombardo et al. | 606/61 |
| 2005/0096657 | A1 | * | 5/2005 | Autericque et al. | 606/69 |
| 2006/0009770 | A1 | * | 1/2006 | Speirs et al. | 606/69 |
| 2007/0010817 | A1 | | 1/2007 | de Coninck | |
| 2008/0147128 | A1 | * | 6/2008 | Fritzinger | 606/304 |
| 2008/0177330 | A1 | * | 7/2008 | Ralph et al. | 606/290 |
| 2008/0279652 | A1 | * | 11/2008 | Mielke | 411/109 |
| 2009/0312803 | A1 | * | 12/2009 | Austin et al. | 606/305 |

(Continued)

OTHER PUBLICATIONS

International Search Report and Written Opinion, PCT/US2013/041419, dated Sep. 24, 2013, 8 pages.

(Continued)

*Primary Examiner* — Christian Sevilla
*Assistant Examiner* — Eric S Gibson
(74) *Attorney, Agent, or Firm* — Baker & McKenzie LLP (57) ABSTRACT

Disclosed embodiments relate to a fastener operable to be received into an opening defined in a plate. The fastener may include a modular sleeve having an actuatable mechanism operable to prevent the rotation of the fastener relative to the plate. The modular sleeve may be moved from a non-actuated first position and an actuated second position to actuate the actuatable mechanism. A portion of the modular sleeve may be accessible from a top side of the head of the fastener through a plurality of channels in the head, and the modular sleeve may be accessible through the plurality of channels in the head in order to actuate the modular sleeve.

9 Claims, 10 Drawing Sheets

(56) References Cited

U.S. PATENT DOCUMENTS

| | | |
|---|---|---|
| 2010/0094356 A1* | 4/2010 | Varela et al. ............... 606/304 |
| 2011/0029023 A1 | 2/2011 | Tornier |
| 2011/0160776 A1* | 6/2011 | Erickson et al. ............ 606/286 |
| 2012/0253407 A1* | 10/2012 | Dunn et al. ................. 606/289 |
| 2013/0310881 A1* | 11/2013 | Klein .......................... 606/305 |

OTHER PUBLICATIONS

Supplementary Partial European Search Report, EP Application No. 13790977.6, dated Jan. 18, 2016, 6 pages.

Extended European Search Report, EP Application No. 13790977.6, dated May 4, 2016, 10 pages.

* cited by examiner

ANTI-BACKOUT MECHANISM FOR ORTHOPEDIC DEVICES

TECHNICAL FIELD

The present disclosure relates generally to orthopedic devices, and more specifically to orthopedic devices having a mechanism to prevent a fastener from backing out.

BACKGROUND

Medical plates and screws have long been used in surgery to repair broken bones. Surgical repair is recommended for complicated fractures that cannot be realigned by nonsurgical methods. This is especially true of fractures that involve joints because poorly aligned joint surfaces may contribute to the development of arthritis over time. When a patient breaks a bone and decides to undergo surgery to fix the bone, a surgeon may make a surgical cut over the bone in order to set the bone in its proper position. Screws and plates can be attached to the bone either temporarily or permanently to help the broken bone heal in the proper position. A plate may be placed across the break and be held in place by two or more screws in order to set the bone and hold the plate in place. It is usually not necessary to remove an internal fixation device unless it is later causing problems for the recipient.

SUMMARY

In an exemplary embodiment of a fastener operable to be received into an opening defined in a plate, the fastener may comprise a head comprising a channel in a circumferential portion of the head, a neck connected to a lower surface of the head, and a body extending from the neck. In an embodiment, the disclosed fastener further comprises a modular sleeve connected to the neck, the modular sleeve comprising an actuatable mechanism operable to move from a non-actuated first position to an actuated second position, wherein when the actuatable mechanism is in the actuated second position, the actuatable mechanism is operable to prevent the rotation of the body relative to the plate.

In an exemplary embodiment of a plate operable to receive a fastener, the fastener comprising a neck and a modular sleeve disposed around the neck, the plate may comprise a top surface, a bottom surface, and at least one aperture extending from the top surface to the bottom surface of the plate along a longitudinal axis. The aperture may comprise a top portion, an intermediate portion, and a bottom portion, and in an embodiment, a diameter of the top portion is greater than a diameter of the intermediate portion, and a diameter of the intermediate portion is greater than a diameter of the bottom portion of the aperture. In an embodiment, at least one groove is defined in the intermediate portion, the at least one groove extending parallel to the longitudinal axis of the aperture.

In accordance with another embodiment of the present disclosure, an orthopedic plate assembly may include a fastener comprising a head comprising a channel in a circumferential portion of the head, a neck connected to a lower surface of the head, and a body extending from the neck. The plate assembly may also include a plate operable to receive the fastener, the plate comprising a top surface, a bottom surface, and at least one aperture extending from the top surface to the bottom surface of the plate along a longitudinal axis. The aperture may comprise a top portion, an intermediate portion, and a bottom portion. In an exemplary embodiment, when the fastener is received in the aperture, the neck of the fastener is disposed within the top and intermediate portions of the aperture, and an actuatable mechanism of the modular sleeve is operable to move along the neck from a non-actuated first position to an actuated second position, the non-actuated first position being within the top portion and the second actuated position being within the intermediate portion. In an embodiment, the aperture of the plate comprises at least one groove defined in the intermediate portion, the at least one groove extending parallel to the longitudinal axis of the aperture, and the actuatable mechanism comprises at least one projection extending from an outer edge portion of the sleeve, the at least one projection and at least one groove being operable to latch onto each other when the actuatable mechanism is in the second actuated position, thereby substantially preventing a rotation of the fastener relative to the plate.

BRIEF DESCRIPTION OF THE DRAWINGS

For a more complete understanding of the present disclosure and its advantages, reference is now made to the following description taken in conjunction with the accompanying drawings, in which like reference numbers indicate like features, and.

DETAILED DESCRIPTION

One of the problems associated with using plates and screws to fix broken bones is that the patient's normal day-to-day movements may cause the screws to back away from the plate, causing discomfort for the patient and also reducing the effectiveness of the plate itself if the plate is able to move independently of the bone beneath it. A locking mechanism may be provided to allow the surgeon to interlock the screws with the plate. In one approach, the surgeon uses a first driving tool to drive the screw through the plate and into the bone and then remove the first driving tool in order to use a second locking tool to access the locking features of the screw and plate. Locking mechanisms that require the surgeon to use two tools increase the length of the surgery, increase the risk of infection by requiring two separate tools, and increase the costs of the surgery by requiring the surgeon to purchase separate driving and locking tools. As such, there is a need for an integrated sleeve lock screw with an anti-backout mechanism that allows the surgeon to complete the locking feature without removing the tool used to drive the screw downward through the plate and into the bone.

The aforementioned need for a screw and integrated locking sleeve may be satisfactorily addressed with using a sleeve lock screw anti-backout mechanism disclosed in this application. Generally, the disclosed embodiments may be applied to any implant where supplemental fixation is applied to an implant is desired to set stand alone interbodies such as bones, vertebrae, joints, or any other suitable portions.

Figures 1, 2:
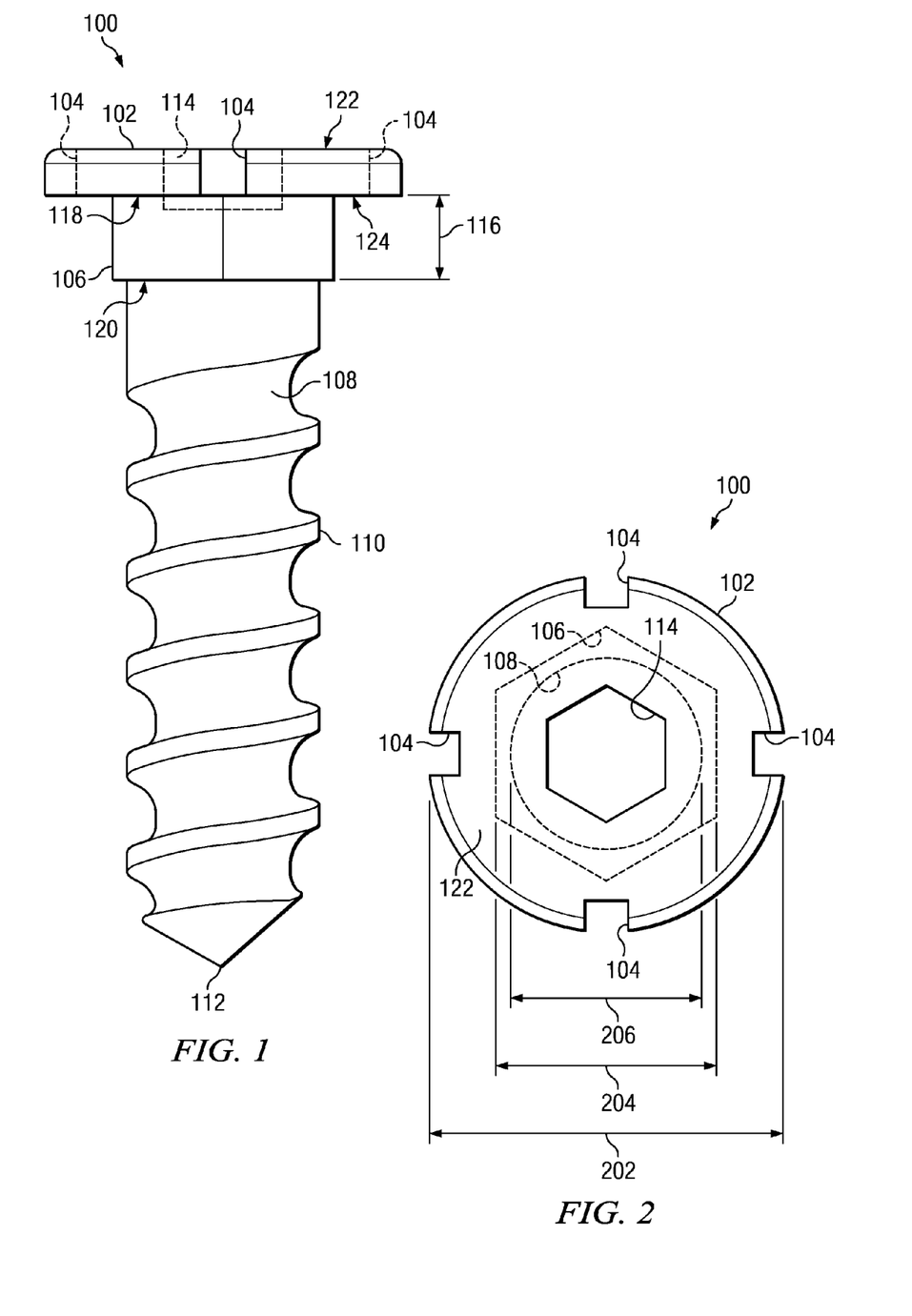
FIG. 1 illustrates a profile view of an exemplary embodiment of a fastener.
FIG. 2 illustrates a cross-sectional top view of the fastener shown in FIG. 1.

FIG. 1 illustrates an exemplary embodiment of a fastener 100. FIG. 2 illustrates a top view of the fastener 100 shown in FIG. 1. In an exemplary embodiment, the fastener 100 may be a screw, although the fastener 100 may also be any other suitable connection devices. The fastener 100 comprises a head 102 having a channel 104 defined therethrough, a neck 106 connected to a lower surface of the head 106, and a body 108 extending from the neck 106. In the illustrated embodiment, a plurality of channels 104 are defined in a circumferential portion of the head 102. As can be seen from the top view in FIG. 2, the plurality of channels 104 may be defined and spaced about the outer circumference of the head 102 of the fastener 100. In one embodiment, there are four channels 104 about the outer circumference, although in other embodiments, there may be different numbers of channels 104. Referring back to FIG. 1, each channel 104 may extend from a top surface 122 of the head 102 to a bottom surface 124 of the head 102 such that the under side of the head 102 would be accessible from above the head 102.

In addition, the head 102 may also comprise a driving recess 114 defined in the top surface 122 of the head 102. The driving recess 114 may be accessible from the top surface 122 of the head 102 of the fastener, and in one embodiment, is hexagonal in shape. In an embodiment, when a tool (not shown) may be inserted into the driving recess 114, and the tool may be operable to rotate the fastener 100 to drive the fastener 100 into a bone (not shown) located below the plate. The driving recess 114 may be configured to have a variety of shapes, including hexagonal, flat, or Phillips style, in order to be used with a variety of driving tools. The driving tool may be configured with a sleeve around the tool that is configured to be received through the plurality of channels 104 to access the under side of the head 102. In another embodiment, the fastener 100 may be driven down by a tool via the plurality of channels 104 in the head and then the same tool can access the locking mechanism. According to one aspect of the present disclosure, the integrated anti-backout mechanism may allow the surgeon to complete the locking feature without removing the driving tool. Other designs require the surgeon to remove the driving tool before being able to access the locking feature.

The neck 106 of the fastener 100 is connected to the bottom surface 124 of the head 102. In an embodiment, the neck 106 is non-circular in shape, such as hexagonal. The neck 106 is configured to receive and mate with a modular sleeve (not shown). The non-circular shape of the neck 106 may prevent the modular sleeve from rotating relative to the neck 106. The neck 106 comprises the neck height 116, defined by the distance from the top surface 118 of the neck 106 to the bottom surface 120 of the neck 106.

The body 108 of the fastener 100 extends from the bottom surface 120 of the neck 106, and in one embodiment, ends at a tip 112. The body 108 may include threads 110 and may be self-threading, although the fastener 100 does not have to be self-threading.

Referring back to FIG. 2, the head 102 comprises the head width 202, the neck 106 comprises the neck width 204, and the body 108 comprises the body width 206. The head width 202 is greater than the neck width 204, and the neck width 204 is greater than the body width 206.

Figure 3:
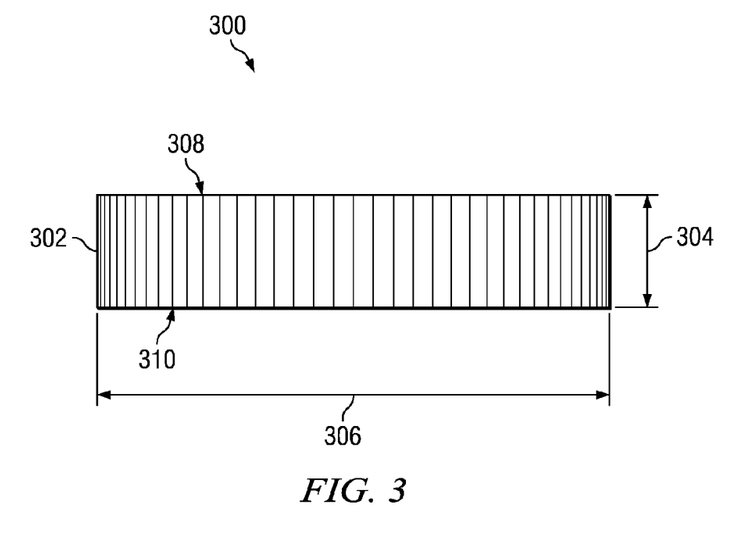
FIG. 3 illustrates a profile view of an exemplary embodiment of a modular sleeve.
Figure 4:
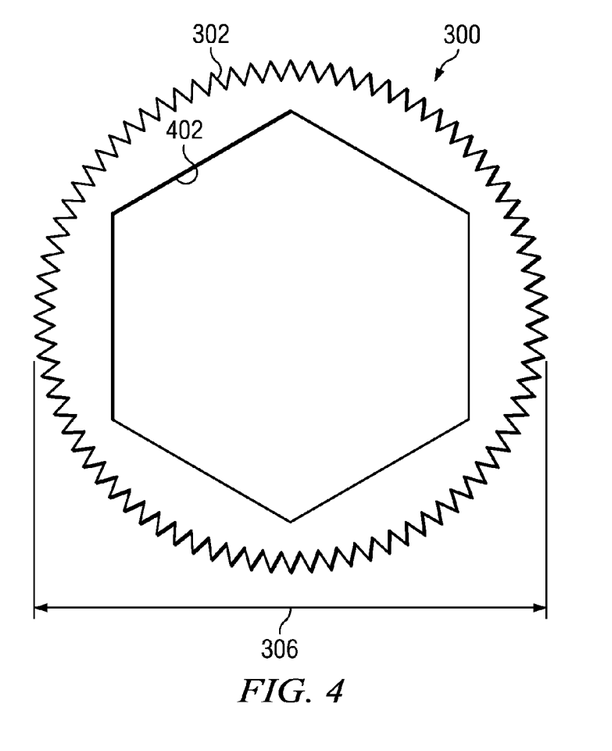
FIG. 4 illustrates a top view of the modular sleeve shown in FIG. 3.

FIG. 3 illustrates a profile view of an exemplary embodiment of a modular sleeve 300. FIG. 4 illustrates a top view of the modular sleeve 300 shown in FIG. 3. Referring to FIGS. 3 and 4, the modular sleeve 300 is operable to be received and mated with the neck 106 of the fastener 100 shown in FIGS. 1 and 2. The modular sleeve 300 may comprise a central opening 402 that has substantially the same shape as the neck 106 of FIGS. 1 and 2. The shape of the central opening 402 of the modular sleeve 300 may be designed to mate with the neck 106 of the fastener 100. The central opening 402 may define a longitudinal axis extending from the top surface 308 of the modular sleeve 300 to the bottom surface 310 of the modular sleeve 300. The central opening 402 may be non-circular in shape, and in one embodiment, the central opening 402 is hexagonal in shape. In such embodiments, the non-circular shape of the central opening 402 may prohibit the modular sleeve 300 from rotating about the neck 106.

The modular sleeve 300 comprises the modular sleeve height 304 and the modular sleeve width 306. The modular sleeve height 304 is defined by the distance between the top surface 308 of the modular sleeve 300 and the bottom surface 310 of the modular sleeve 300. Referring back to FIG. 1, the neck height 116 may be greater than the modular sleeve height 304 of FIG. 3 such that the modular sleeve 300 can longitudinally slide in an axial direction away from the head 102 on the neck 106 from a non-actuated first position to an actuated second position. Referring back to FIG. 3, the modular sleeve width 306 is less than the head width 202 and greater than the neck width 204 of FIG. 2.

The modular sleeve 300 comprises a latch mechanism 302. In some embodiments, the latch mechanism may comprise a plurality of projections 302 extending from an outer edge portion of the modular sleeve 300. In one embodiment, the projections 302 extend vertically along the outer edge portion of the modular sleeve 300 and parallel with the longitudinal axis defined in the central opening 402 of the modular sleeve 300. In FIGS. 3 and 4, the modular sleeve 300 is configured to resemble a spur gear and includes a plurality of projections 302 extending vertically along the entire outer edge portion of the modular sleeve 300.

Figure 5:
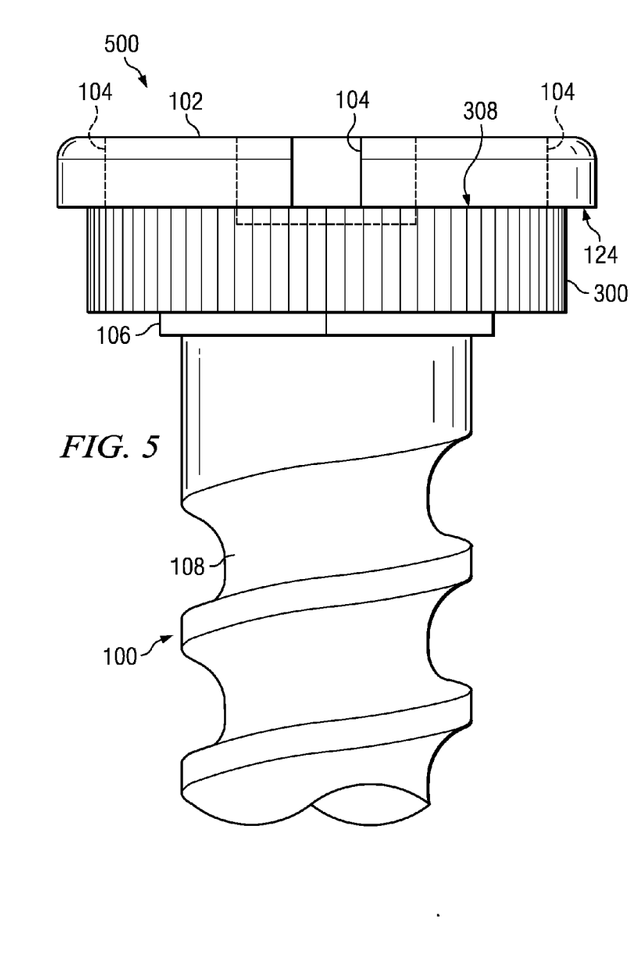
FIG. 5 illustrates a side view of the fastener shown in FIG. 1 receiving the modular sleeve shown in FIG. 3 in a non-actuated first position.

FIG. 5 illustrates a side view of the fastener 100 shown in FIG. 1 receiving the modular sleeve 300 shown in FIG. 3 in a non-actuated first position 500. In the non-actuated first position 500, the fastener 100 is inserted through the central opening (not shown) of the modular sleeve 300, which may be adjacent or abutting the bottom surface 124 of the head 102. As such, the modular sleeve 308 may be accessible from the top side of the head 102 through the plurality of channels 104 defined in the head 102. The modular sleeve 300 may be maintained at the first position 500 by a friction type fit around the neck 106. As discussed above, the shape of the neck 106 and the shape of the opening 402 may be configured such that the modular sleeve 300 cannot rotate about the neck 106 of the fastener 100, but the modular sleeve 300 can slide axially along the neck 106 of the fastener 100.

Figure 6:
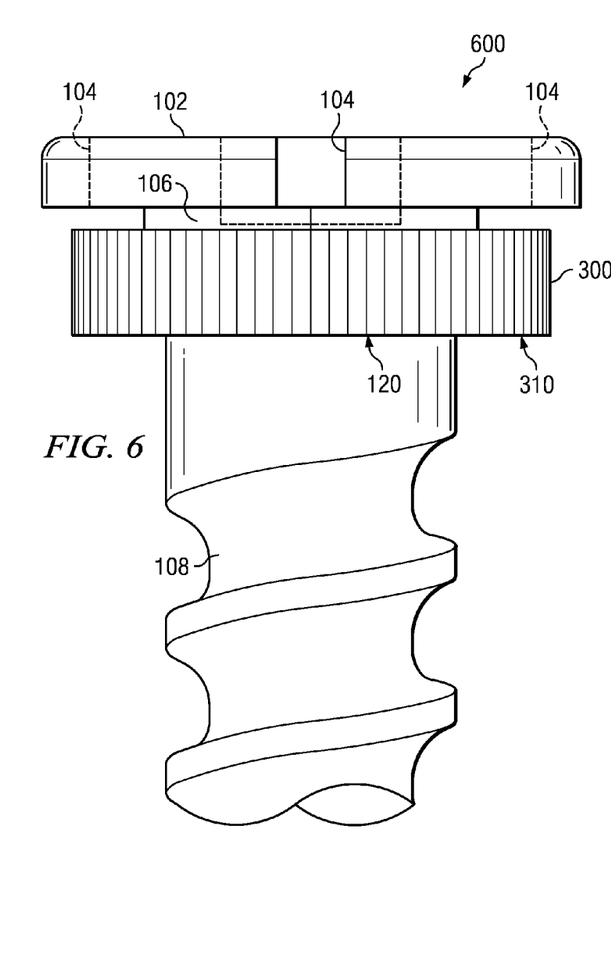
FIG. 6 illustrates a side view of the fastener shown in FIG. 5 receiving the modular sleeve shown in FIG. 3 in an actuated second position.

FIG. 6 illustrates a side view of the fastener 100 shown in FIG. 1 receiving the modular sleeve 300 shown in FIG. 3 in an actuated second position 600. In the actuated second position 600, the modular sleeve 300 has been moved downwardly along the neck 106 and is spaced away from the head 102 of the fastener 100. As illustrated in FIG. 6, the bottom surface 310 of the modular sleeve 300 may be flush with the bottom surface 120 of the neck 106. Referring to FIGS. 5 and 6, the modular sleeve 300 may be deployed from the non-actuated first position 500 to the actuated second position 600 by longitudinally sliding the modular sleeve 300 along the neck 106 of the fastener 100 with a tool inserted through the plurality of channels 104 in the head 102.

Figure 7:
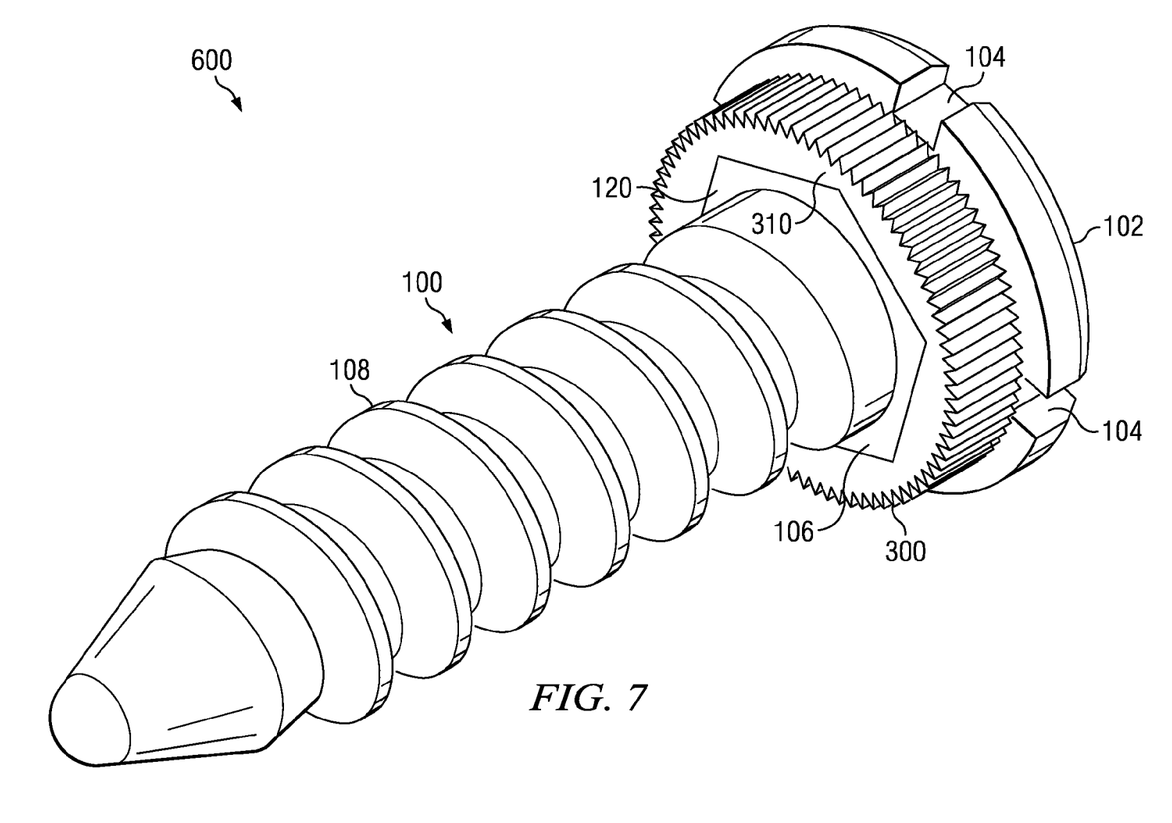
FIG. 7 illustrates a perspective view of the fastener and modular sleeve shown in FIG. 6.

FIG. 7 illustrates a perspective view of the actuated second position 600 shown in FIG. 6. In the actuated second position 600, the modular sleeve 300 has been deployed by a tool via the plurality of channels 104 in the head 102 such that the bottom surface 310 of the modular sleeve 300 is spaced away from the head 102 of the fastener 100.

Figure 8:
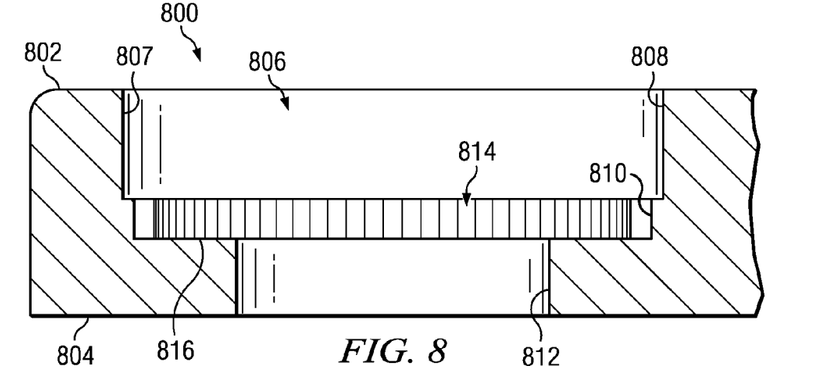
FIG. 8 shows a cross-sectional view of an exemplary embodiment of a plate.

FIG. 8 shows a cross-sectional view of an exemplary embodiment of a plate 800. The plate 800 includes a top surface 802, a bottom surface 804, and an aperture 806 having a top portion 808, an intermediate portion 810, and a bottom portion 812. The intermediate portion 810 may include an inner sidewall 807 and a bottom surface 816. A plurality of grooves 814 may be defined in the inner sidewall 807. The plate 800 may include one or more apertures 806 extending from the top surface 802 to the bottom surface 804. Each aperture 806 may have a central longitudinal axis defined therein.

Each of the grooves 814 may extend vertically and parallel with the central longitudinal axis of the aperture 806, and the number of grooves 814 defined in the intermediate portion 810 of the inner sidewall 807 may be the same as the number of projections 302 extending from the modular sleeve 300 of FIGS. 3-4 or may be only one groove 814. The one or more grooves 814 may be configured to mesh with the projections 302 extending from the modular spacer 300.

It is to be appreciated that the number and size of projections 302 in the modular sleeve 300 may be varied. Advantageously, the more projections 302 and groves 814, the easier it is for the modular sleeve 300 to mesh with the intermediate section 810 when the fastener 100 and modular sleeve 300 are received into the plate 800. In an embodiment, incorporating a larger number of smaller projections 302 may improve the convenience of positioning the fastener 100 before driving the fastener 100 into the bone. With a large number of small projections 302, the surgeon would just have to drive the fastener 100 and modular sleeve 300 through the plate and the small projections 302 will easily align with an equal number of small groves defined in the plate, regardless of the orientation of the fastener 100.

Figure 9:
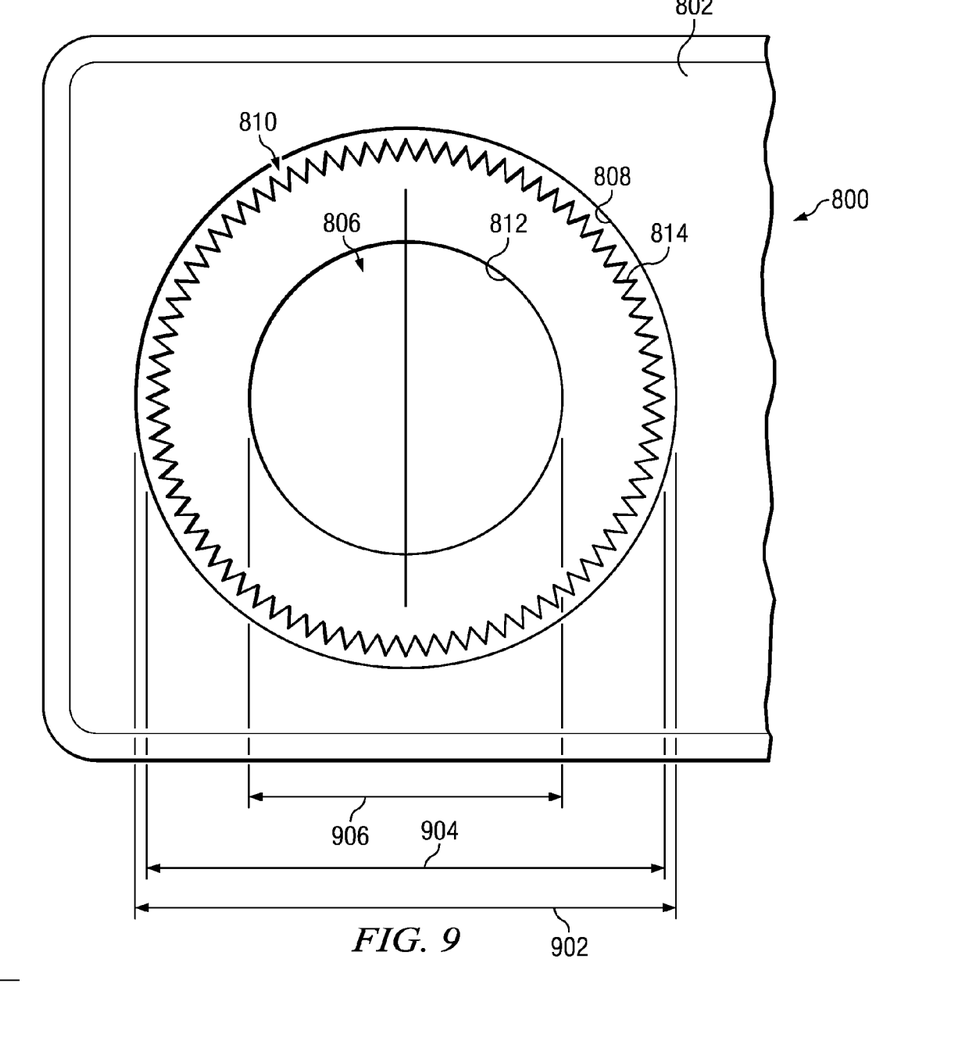
FIG. 9 shows a top view of the plate shown in FIG. 8.
Figure 10:
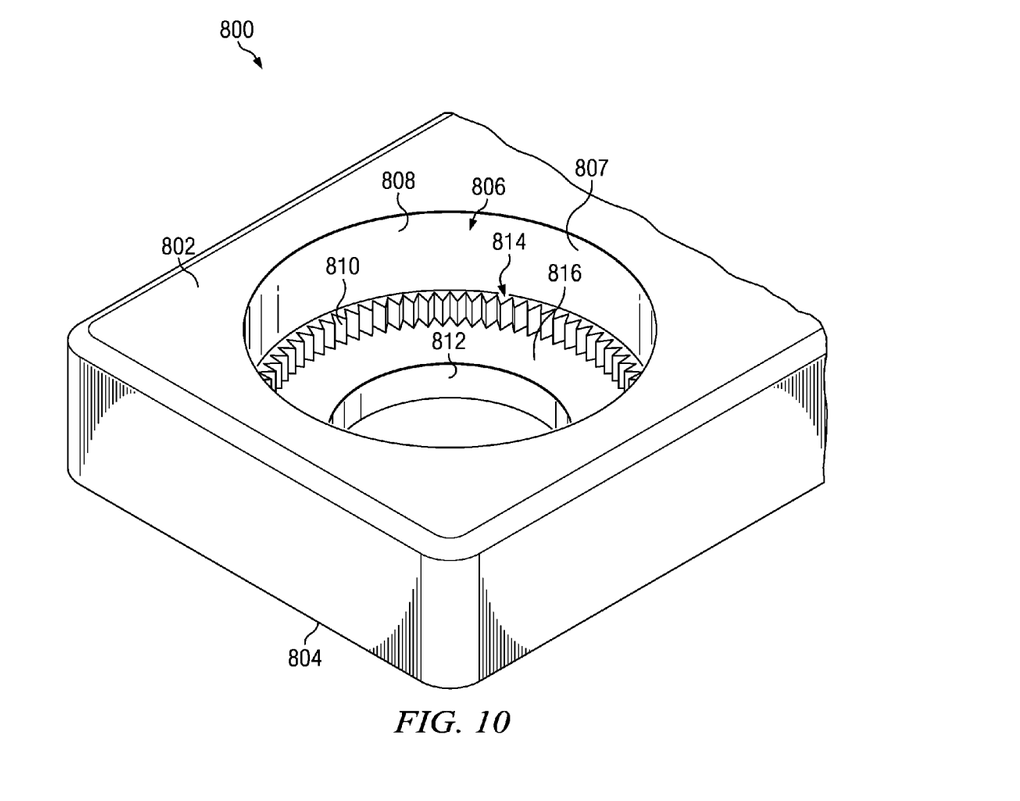
FIG. 10 shows a perspective view of the plate shown in FIG. 8.

FIG. 9 shows a top view of the plate 800 shown in FIG. 8. FIG. 10 shows a perspective view of the plate 800 shown in FIG. 8. The plate 800 includes a top portion diameter 902, an intermediate portion diameter 904, and a bottom portion diameter 906. The top portion diameter 902 may be greater than the intermediate portion diameter 904, and the intermediate portion diameter 904 may be greater than the bottom portion diameter 906. Referring now to FIG. 2, the bottom portion diameter 906 may be greater than or equal to the body width 206. Referring now to FIGS. 3 and 4, the top portion diameter 902 and the intermediate portion diameter 904 may be greater than or equal to the modular sleeve width 306.

Referring to FIGS. 8-10, in each aperture 806, the top portion 808 is configured to receive the combination fastener 100 and the modular sleeve 300 when the modular sleeve 300 is in the non-actuated first position 500. The top portion 808 and the intermediate portion 810 are configured to receive the modular sleeve 300 when the modular sleeve 300 is in the actuated second position 600 and the projections 302 of the modular sleeve 300 are meshed with the grooves 814 of the intermediate portion 810. The modular sleeve 300 is prevented from longitudinally sliding beyond the intermediate portion 810 by the bottom surface 816 of the intermediate portion 810. The bottom portion 812 is configured to receive the body 108 of the fastener 100.

Figure 11:
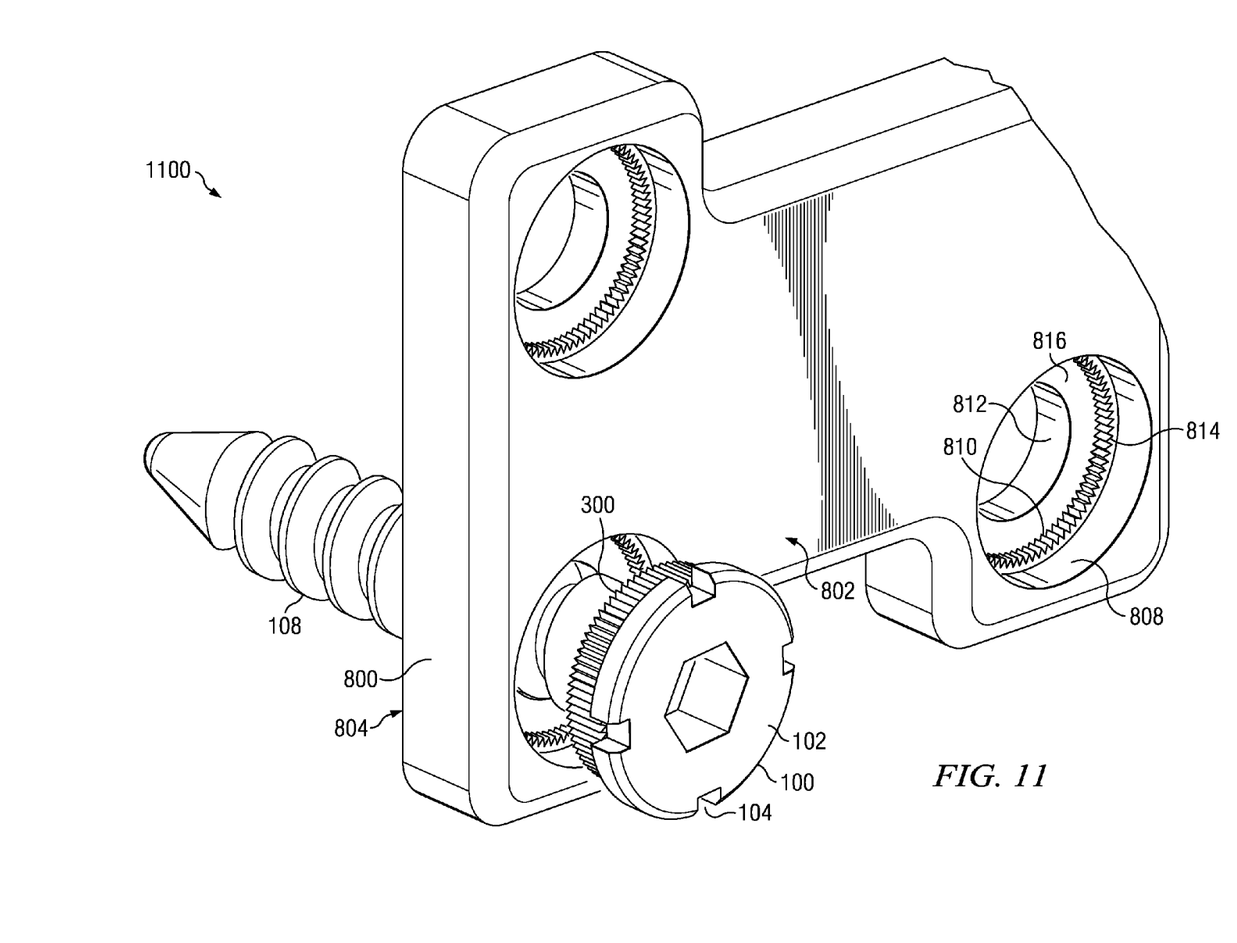
FIG. 11 shows a perspective view of the plate shown in FIG. 10 receiving a fastener and a modular sleeve.

FIG. 11 shows a perspective view of the plate 800 shown in FIG. 8 receiving a fastener 100 and a modular sleeve 300. Referring to FIGS. 8-10, the one or more apertures 806 are each configured to receive the fastener 100 and modular spacer 300 illustrated in FIGS. 5-7. The non-circular shapes of the neck 106 of the fastener 100 and the central opening 402 in the modular sleeve 300 prevent the modular sleeve 300 from rotating about the neck 106. After the modular sleeve 300 initially receives the fastener 100 through its central opening 402 and the modular sleeve 300 is in the non-actuated first position 500 along the neck 106 of the faster 100, the fastener 100 and modular sleeve 300 are ready to be inserted through the aperture 806 of the plate 800.

Figure 12:
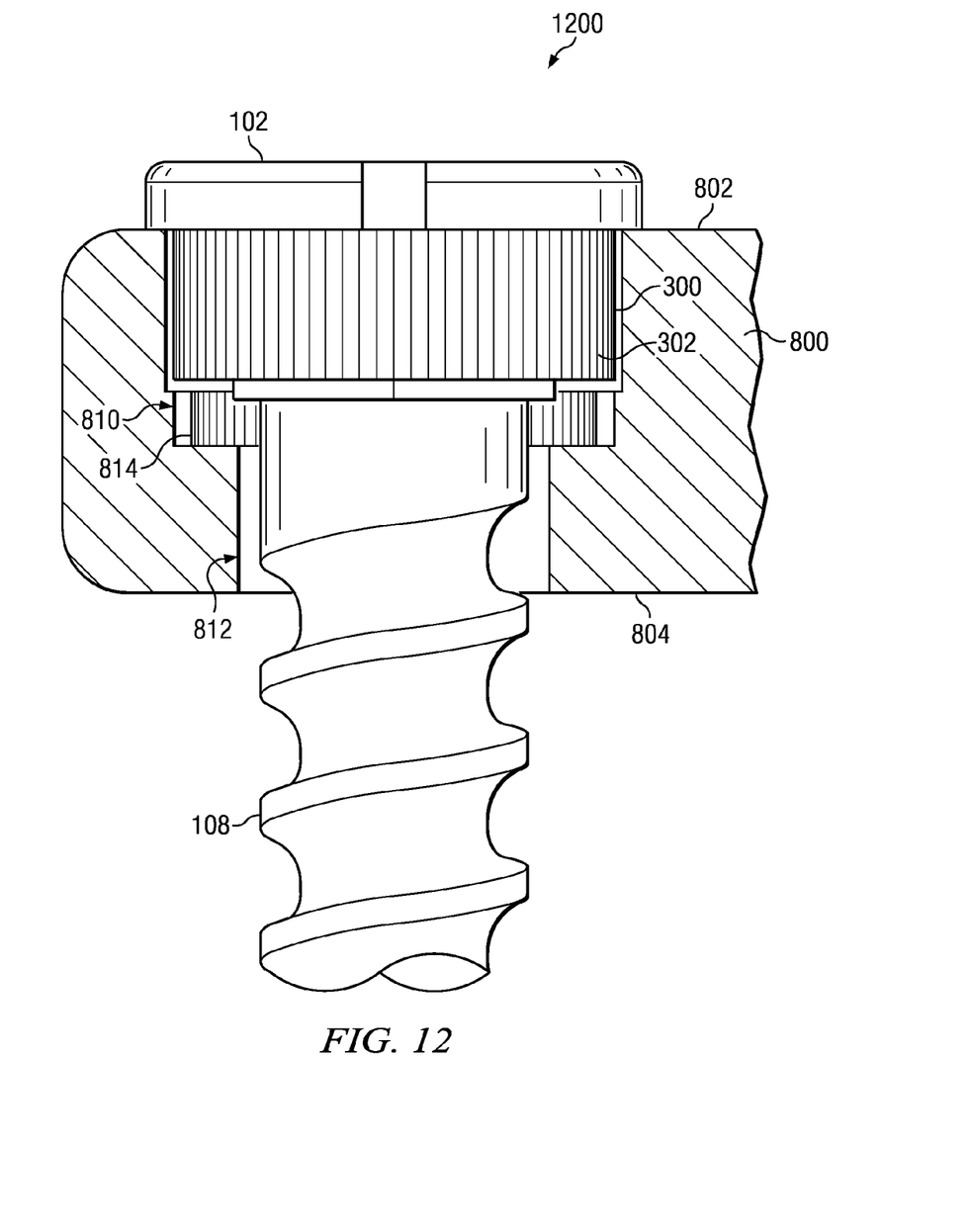
FIG. 12 shows a cross-sectional view of the plate shown in FIG. 11 receiving the fastener and the modular sleeve in the non-actuated first position.

The body 108 of the fastener 100 is inserted through the top surface 802 of the plate 800 via the aperture 806, received through the bottom portion 812, and driven down until the head 102 of the fastener 100 is bottomed out against the top surface 802 of the plate 800. When the head 102 of the fastener 100 has bottomed out against the top surface 802 of the plate 800, the sleeve 300 remains in the non-actuated first position 500 and is received in the top portion 808. Meanwhile, the body 108 of the fastener 100 is received through the bottom portion 812. FIG. 12 shows a cross-sectional view of the plate shown in FIG. 11 receiving the fastener and the modular sleeve in the non-actuated first position 500.

After the head 102 of the fastener 100 bottoms out against the top surface 802 of the plate 800, the modular sleeve 300 is ready to be deployed from the non-actuated first position 500 to the actuated second position 600. Doing so would allow an actuatable mechanism of the modular sleeve 300 to prevent the fastener 100 and modular sleeve 300 from backing away from the plate 800. The actuatable mechanism is deployed via the channels 104 in the head 102 of the fastener 100 by inserting the tool into the channels 104 and longitudinally sliding the modular sleeve 300 along the neck 106 in an axial direction away from the head 102. Advantageously, the same tool can be configured to drive down the fastener 100 and deploy the modular sleeve 300 into the actuated second position 600.

Figure 13:
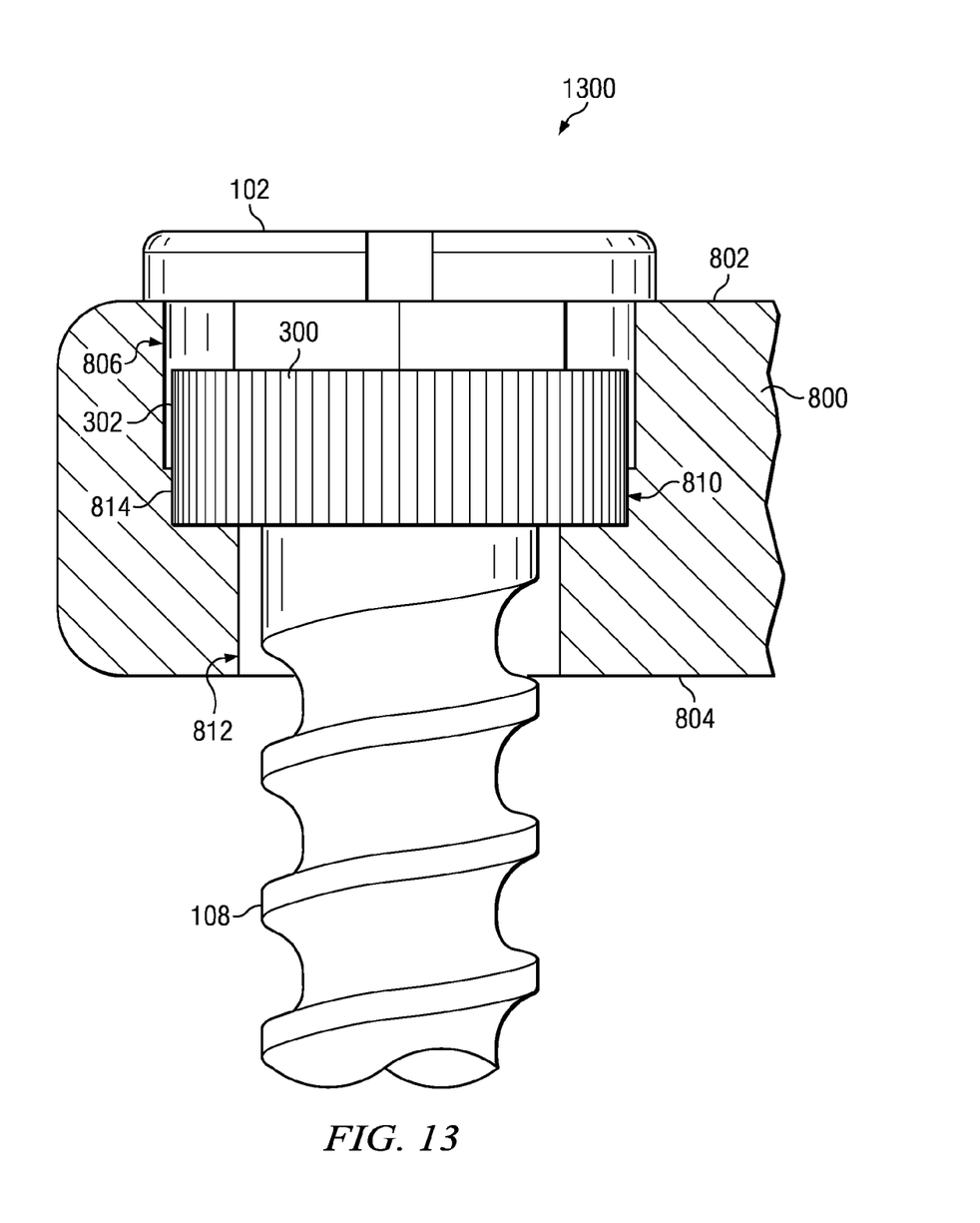
FIG. 13 shows a cross-sectional view of the plate shown in FIG. 12 receiving the fastener and the modular sleeve in the actuated second position.

When a lower portion of the modular sleeve 300 is received into the intermediate portion 810, the projections 302 along the outer edge of the modular sleeve 300 mesh with the grooves 814 defined in the intermediate portion 810 of the inner sidewall 807, while the remainder of the modular sleeve 300 is still received into the top portion 808. As such, modular sleeve 300 is in the actuatable second position 600. FIG. 13 shows a cross-sectional view of the plate shown in FIG. 12 receiving the fastener and the modular sleeve in the actuated second position 600.

Figure 14:
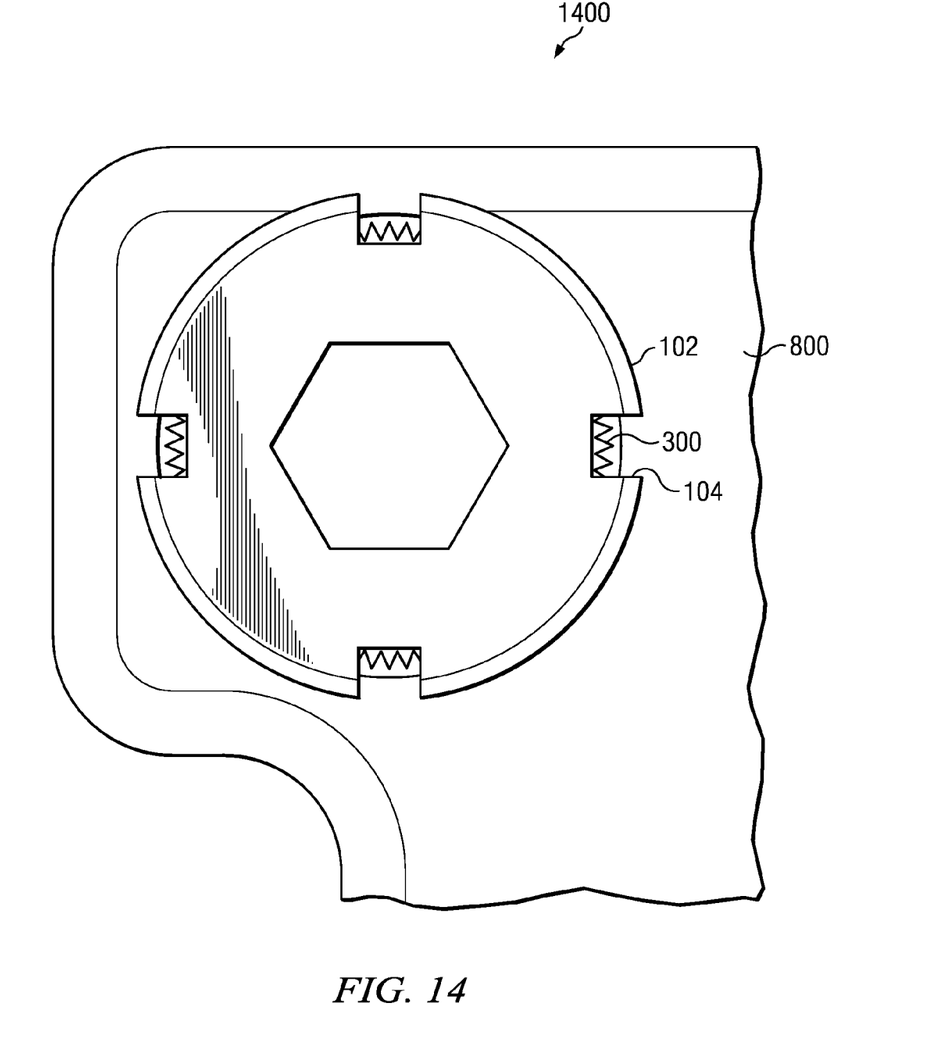
FIG. 14 shows a top view of the plate shown in FIG. 11 receiving the fastener and the modular sleeve.

The meshing of the projections 302 of the modular sleeve 300 with the grooves 814 in the intermediate portion 810 locks the fastener 100 and modular sleeve 300 into the plate 800 and prevent the fastener 100 and modular sleeve 300 from rotating relative to the plate 800. The modular sleeve 300 will be retained between the fastener 100 and the plate 800 after deployment between the neck 106 of the fastener 100 and the central opening 402 of the modular sleeve 300 and by meshing between the projections 302 of the modular sleeve 300 and the grooves 814 of the intermediate portion 810 in the plate 800. FIG. 14 shows a top view of the plate 800 having received the fastener 100 and the modular sleeve 300 shown in FIG. 13.

Advantageously, the integrated locking mechanism as described in the present disclosure allows a surgeon to complete the locking of the fastener 100, sleeve 300, and the plate 800 to each without removing the tool used to drive the fastener 100 downward. In one embodiment, this is accomplished by using a tool configured to rotate and drive down the combination fastener and modular spacer 1100 into the plate 800 via the openings in the head 102 comprising the plurality of channels 104. Once the combination fastener and modular spacer 1400 has been fully driven down and the head 102 has bottomed out against the top surface 802 of the plate 800, the same tool can then be used to deploy the actuatable mechanism from the non-actuated first position 500 to the actuated second position 600 via the same channels 104.

In the disclosed embodiments, the fastener 100, the modular sleeve 300, and the plate 800 may all be manufactured from an implantable grade metal such as stainless steel or a titanium alloy. Multiple sizes of fasteners 100 may be used, as is required by the specific bone repair application, although the size of the fastener 100 determines the size of the modular sleeve 300 and accordingly the size of the aperture 806 in the plate 800.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. An orthopedic plate assembly, comprising:
    a fastener comprising:
        a head comprising a channel in a circumferential portion of the head;
        a neck connected to a lower surface of the head, the neck having a neck height defined by a distance from a top surface of the neck to a bottom surface of the neck;
        a body extending from the neck; and
        a modular sleeve connected to the neck, wherein the modular sleeve comprises at least one projection extending from an upper surface of the modular sleeve to a lower surface of the modular sleeve along a longitudinal axis, the modular sleeve having a modular sleeve height defined by the distance between the upper surface of the modular sleeve and the lower surface of the modular sleeve, the modular sleeve height being less than the neck height;
    a plate operable to receive the fastener, the plate comprising:
        a top surface;
        a bottom surface; and
        at least one aperture extending from the top surface to the bottom surface of the plate along the longitudinal axis, the aperture comprising a top portion, an intermediate portion, and a bottom portion, wherein the intermediate portion comprises at least one groove defined along the longitudinal axis therewithin;
    wherein when the fastener is received in the aperture, the neck of the fastener is disposed within the top and intermediate portions of the aperture, such that, based in part upon the difference between the neck height and the modular sleeve height, the modular sleeve is operable to move longitudinally along the neck from a non-actuated first position to an actuated second position, the non-actuated first position being within the top portion and the actuated second position being within the intermediate portion;
    wherein when the modular sleeve is in the non-actuated first position, the fastener can rotate freely relative to the plate; and
    wherein when the modular sleeve is in the actuated second position, the at least one projection of the modular sleeve is operable to mesh with the at least one groove of the intermediate portion of the at least one aperture and the fastener is prevented from rotation relative to the plate;
    wherein the modular sleeve is operable to move longitudinally between the non-actuated first position to the actuated second position when the bottom surface of the head bottoms out against a surface of the plate.

2. The orthopedic plate assembly of claim 1, wherein the body comprises a threaded portion.

3. The orthopedic plate assembly of claim 1, wherein the neck is non-circular in shape.

4. The orthopedic plate assembly of claim 1, wherein the neck is hexagonal in shape.

5. The orthopedic plate assembly of claim 1, wherein the modular sleeve comprises a central opening operable to receive and mate with the neck.

6. The orthopedic plate assembly of claim 1, wherein a portion of the modular sleeve is accessible from a topside of the head through the channel in the head.

7. The orthopedic plate assembly of claim 1, wherein the modular sleeve is actuatable from the non-actuated first position to the actuated second position by longitudinally sliding the modular sleeve along the neck away from the head.

8. The orthopedic plate assembly of claim 1, wherein the head comprises a plurality of channels spaced from each other circumferentially.

9. The orthopedic plate assembly of claim 1, wherein a diameter of the top portion of the aperture is greater than a diameter of the intermediate portion of the aperture, and a diameter of the intermediate portion of the aperture is greater than a diameter of the bottom portion of the aperture.

* * * * *